United States Patent [19]
Kitamura et al.

[11] Patent Number: 4,886,807
[45] Date of Patent: Dec. 12, 1989

[54] NOVEL PYRIMIDOPYRIMIDINE DERIVATIVE, PROCESS FOR PRODUCING IT AND PHARMACEUTICAL COMPOSITION

[75] Inventors: Norihiko Kitamura; Akimoto Ohnishi, both of Katoh, Japan

[73] Assignee: Nippon Zoki Pharmaceutical Co., Ltd., Osaka, Japan

[21] Appl. No.: 277,447

[22] Filed: Nov. 29, 1988

Related U.S. Application Data

[63] Continuation of Ser. No. 726,618, Apr. 24, 1985, abandoned.

[30] Foreign Application Priority Data

Apr. 24, 1988 [JP] Japan .................................. 59-83557

[51] Int. Cl.$^4$ .................. C07D 471/04; A01R 31/505
[52] U.S. Cl. ..................................... 514/258; 544/256
[58] Field of Search ......................... 544/256; 514/258

[56] References Cited

PUBLICATIONS

Hirota et al., Chemical Abstracts, vol. 102:95601h, 1985.
Tominaga et al., Heterocycles, vol. 12, No. 4, pp 503–504, (1979).
Kokel et al., Bull. Soc. Chim. Belg., vol. 89, No. 8, pp. 651–657, (1980).
Noda et al, Chemical Abstracts, vol. 87:53365a, (1977).
Noda et al., Chemical Abstracts, vol. 87:53356y, (1977).
Noda et al., Chemical Abstracts, vol. 87:68404m, (1977).
Noda et al., Chemical Abstracts, vol. 87:201572h, (1977).
Krell et al., "Preclinical Evaluation of Anti-Allergic Agents", Journal of Pharmaceutical Sciences, 69, No. 2, pp. 239–243 (Feb. 1980).

Primary Examiner—Robert Gerstl
Attorney, Agent, or Firm—Birch, Stewart, Kolasch & Birch

[57] ABSTRACT

Pyrimidopyrimidine derivatives having the general formula

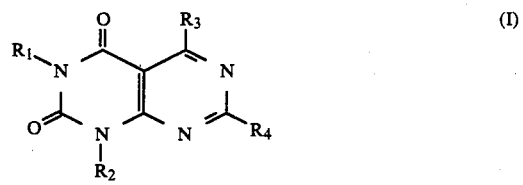

wherein
$R_1$ is an alkyl group;
$R_2$ is an alkyl or phenyl group;
$R_3$ is a hydrogen atom, an alkyl or lower alkylamino group; and
$R_4$ is a hydrogen atom, an alkyl, halogenated lower alkyl, phenyl, amino or lower alkylamino group;

and pharmaceutically acceptable salts thereof. These compounds are useful as anti-allergic agents, for example, for the treatment of bronchial asthma, urticaria, allergic rhinitis, allergic dermatoses or allergic conjunctivitis.

4 Claims, No Drawings

NOVEL PYRIMIDOPYRIMIDINE DERIVATIVE, PROCESS FOR PRODUCING IT AND PHARMACEUTICAL COMPOSITION

This application is a continuation, of application Ser. No. 726,618 filed on Apr. 24, 1985, now abandoned.

BACKGROUND OF THE INVENTION

The present invention is concerned with novel pyrimidopyrimidine derivatives, pharmaceutically acceptable salts thereof, a process for producing then and pharmaceutical compositions containing then as an active ingredient.

It is known that the so-called "chemical mediator", i.e. histamine, serotonin or SRS-A, plays an important role in the appearance of various allergic symptoms in the human body. Thus, since the drug which antagonizes such biochemical substances and/or inhibits their release would be useful for treating or preventing allergic diseases, some compounds have been synthesized and tested in the field so far.

As a result of investigations upon a drug acting on allergic diseases, the inventors have found that the pyrimidopyrimidine derivative of the present invention has an excellent anti-allergic effect.

An object of the present invention is to provide novel pyrimidopyrimidine derivatives and pharmaceutically acceptable salts thereof which are useful for treating or preventing allergic diseases as well as low toxicity and less side effects.

Another object of the invention is to provide a process for producing pyrimidopyrimidine derivatives or pharmaceutically acceptable salts thereof.

A further object of the invention is to provide a pharmaceutical composition containing at least one of the pyrimidopyrimidine derivatives or pharmaceutically acceptable salts thereof as an active ingredient.

DETAILED DESCRIPTION OF THE INVENTION

Pyrimidopyrimidine derivatives of the present invention are represented by the following general formula (I):

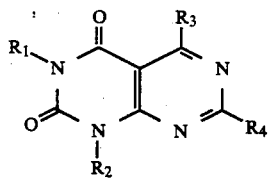

wherein
$R_1$ is an alkyl group;
$R_2$ is an alkyl or phenyl group;
$R_3$ is a hydrogen atom, an alkyl or lower alkylamino group; and
$R_4$ is a hydrogen atom, an alkyl, halogenated lower alkyl, phenyl, amino or lower alkylamino group.

$R_1$ represents a straight or branched alkyl group having 1 to 10 carbon atoms, such as methyl, ethyl, n-propyl, iso-propyl, n-butyl, iso-butyl, sec-butyl, tert-butyl, pentyl, hexyl, heptyl, octyl, nonyl or decyl group, preferably having 1 to 4 carbon atoms such as methyl, ethyl, propyl or butyl group.

$R_2$ represents a straight or branched alkyl group having 1 to 10 carbon atoms, such as methyl, ethyl, n-propyl, iso-propyl, n-butyl, iso-butyl, sec-butyl, tert-butyl, pentyl, hexyl, heptyl, octyl, nonyl or decyl group, preferably having 1 to 4 carbon atoms such as methyl, ethyl, propyl or butyl group; or phenyl group.

$R_3$ represents a hydrogen atom; an amino group; or an amino group substituted by a straight or branched alkyl group having 1 to 4 carbon atoms, such as methyl, ethyl, n-propyl, iso-propyl, n-butyl, iso-butyl, sec-butyl or tert-butyl group, preferably substituted by methyl or ethyl group.

$R_4$ represents a hydrogen atom; an alkyl group, e.g. a straight or branched alkyl group having 1 to 10 carbon atoms, such as methyl, ethyl, n-propyl, iso-propyl, n-butyl, iso-butyl, sec-butyl, tert-butyl, pentyl, hexyl, heptyl, octyl, nonyl or decyl group, preferably having 1 to 4 carbon atoms such as methyl, ethyl, propyl, butyl group; an alkyl group as above substituted by one or more halogen atoms such as trifluoromethyl, fluoromethyl, chloromethyl, fluoroethyl or chloroethyl, preferably a straight or branched alkyl group having 1 to 3 carbon atoms substituted by fluorine or chlorine such as trifluoromethyl; phenyl group; amino group; an amino group substituted by a straight or branched lower alkyl group having 1 to 4 carbon atoms such as methyl, ethyl, n-propyl, iso-propyl, n-butyl, iso-butyl, sec-butyl or tert-butyl group, preferably substituted by methyl or ethyl group.

Preferred compounds of the invention are as follows:
7-phenyl-1,3-dimethylpyrimido[4,5-d]pyrimidine-2,4-dione,
1,3,7-trimethylpyrimido[4,5-d]pyrimidine-2,4-dione,
7-trifluoromethyl-1,3-dimethylpyrimido[4,5-d]pyrimidine-2,4-dione,
1,3-dimethylpyrimido[4,5-d]pyrimidine-2,4-dione,
7-amino-1,3-dimethylpyrimido[4,5-d]pyrimidine-2,4-dione,
7-amino-1-phenyl-3-methypyrimido[4,5-d]pyrimidine-2,4-dione,
7-methylamino-1,3-dimethylpyrimido[4,5-d]pyrimidine-2,4-dione,
5-amino-1,3-dimethylpyrimido[4,5-d]pyrimidine-2,4-dione,
5-amino-1,3-diethylpyrimido[4,5-d]pyrimidine-2,4-dione,
5-amino-1-iso-butyl-3-methylpyrimido[4,5-d]pyrimidine-2,4-dione,
5-amino-1,3,7-trimethylpyrimido[4,5-d]pyrimidine-2,4-dione,
5-amino-1,3-dimethyl-7-phenylpyrimido[4,5-d]pyrimidine-2,4-dione,
5,7-diamino-1,3-dimethylpyrimido[4,5-d]pyrimidine-2,4-dione,
5-methyamino-1,3-dimethylpyrimido[4,5-d]pyrimidine-2,4-dione,
7-amino-1,3-diethylpyrimido[4,5-d]pyrimidine-2,4-dione,
7-amino-1-isobutyl-3-methylpyrimido[4,5-d]pyrimidine-2,4-dione, Pyrimidopyrimidine derivatives of the present invention also include pharmaceutically acceptable salts of the compound of the above formula (I), for example, salts with alkali metal such as lithium, sodium or potassium, alkaline-earth metal such as calcium or magnesium, and other metals such as aluminum or salt as acid addition with an inorganic acid such as hydrochloric acid, sulfuric acid, nitric acid, hydrobromic acid, phosphoric acid, perchloric acid, thiocyanic acid or boric acid, or an organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic or cinnamic acid, or salt with an organic base such as ammonia, trimethylamine, triethylamine or tris(hydroxymethyl)aminomethane.

These salts can be produced from free pyrimidopyrimidine derivative or converted with each other in the usual way.

When optical isomers exist in the compounds of the present invention, the invention includes any of the dl-, d- and l-isomers.

The compounds of the present invention is produced as follows: (Each value of $R_1$, $R_2$, $R_3$ and $R_4$ in the general formula (II), (III), (i) through (xiii) has the same meaning as in the general formula (I).)

A compound having the general formula (II):

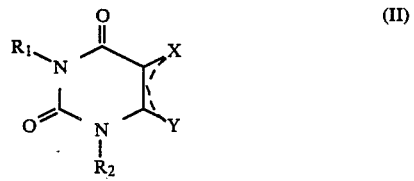
(II)

wherein
$R_1$ is an alkyl group;
$R_2$ is an alkyl or phenyl group;
X is a cyano or di-lower-alkylaminomethylene group;
Y is a halogen atom, an amino, di-lower-alkylaminomethyleneamino, or imino group; and a bond with dotted line indicates a single or double bond;
when the bond between the 5- and 6-position is a single bond, X is a di-lower-alkylaminomethylene group and Y is an imino group;
is reacted with a compound having the general formula (III):

  (III)

wherein
Z is

a lower alkyl or hydroxy group;
A is an oxygen, sulfur atom or an imino group; and
$R_4$ is a hydrogen atom, an alkyl, halogenated lower alkyl, phenyl, amino or lower alkylamino group;
to give a pyrimidopyrimidine derivative having the general formula (I):

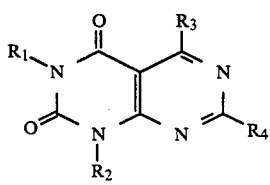
(I)

wherein
$R_1$ is an alkyl group;
$R_2$ is an alkyl or phenyl group;

$R_3$ is a hydrogen atom, an alkyl or lower alkylamino group; and
$R_4$ is a hydrogen atom, an alkyl, halogenated lower alkyl, phenyl, amino or lower alkylamino group.

When Z is a hydroxy group, the obtained compound is reduced to give the compound of formula (I).

In the formula (II), X is a cyano or aminomethylene group substituted by a lower alkyl group having 1 to 4 carbon atoms preferably dimethylaminomethylene group; Y is a halogen atom preferably chlorine, an amino, aminomethyleneamino group substituted by a lower alkyl group having 1 to 4 atoms preferably dimethylaminomethyleneamino group. Additionally when a bond with a dotted line between the 5- and 6-position is a single bond, X is a di-lower-alkylaminomethylene group and Y is an imino group; and when the bond is a double bond, X and Y are other than the above groups.

The process for producing the compound of the present invention can be divided into three ways as follows:

Method (I): 1,3,7-trisubstituted pyrimidopyrimidine derivative obtained by reacting 6-imino-5-di-lower-alkylaminomethylene-5,6-dihydrouracil derivative and a carbamoyl derivative, thiocarbamoyl derivative or amidine A compound having the general formula (i):

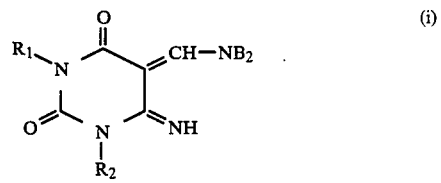
(i)

wherein
$R_1$ is an alkyl group; and
$R_2$ is an alkyl or phenyl group;
B is a lower alkyl group having 1 to 4 carbon atoms;
is reacted with a compound having the general formula (ii):

(ii)

wherein
A is an oxygen, sulfur atom or an imino group; and
$R_4$ is a hydrogen atom, an alkyl, halogenated lower alkyl, phenyl, amino or lower alkylamino group;
to give an intended compound having the general formula (iii):

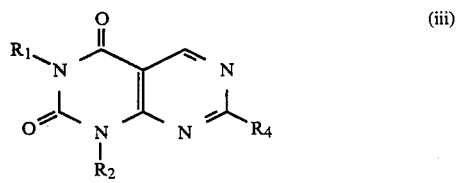
(iii)

wherein
$R_1$ is an alkyl group;
$R_2$ is an alkyl or phenyl group; and
$R_4$ is a hydrogen atom, an alkyl, halogenated lower alkyl, phenyl, amino or lower alkylamino group.

To carry out the above reaction, (a) when A is an oxygen atom; the reaction is carried out in an appropriate inert solvent or without using a solvent for one to several hours at room temperature or with heating at an appropriate temperature or under reflux.

(b) when A is a sulfur atom; the reaction is carried out in an appropriate solvent such as ethanol in the presence of a base such as sodium ethoxide, for one to several hours with heating at an appropriate temperature or under reflux.

(c) when A is an imino group; the reaction is carried out in an appropriate solvent such as ethanol in the presence of a base such as sodium ethoxide, for one to several hours with heating at an appropriate temperature or under reflux.

The above mentioned compound of the formula (i) as a starting material can easily be produced as follows:

1,3-disubstituted 6-aminouracil derivative having the general formula (iv):

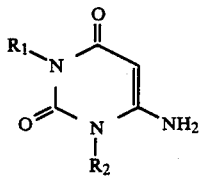

(iv)

wherein
$R_1$ is an alkyl group; and
$R_2$ is an alkyl or phenyl group;
is reacted according to the so-called Vilsmeier reaction, for example, with dialkylformamide and phosphorus oxychloride to give 6-imino-5-di-lower-alkylaminomethylene-5,6-dihydrouracil derivative of the formula (i).

To carry out the reaction, the compound of the formula (iv) is dissolved or suspended in di-lower-alkylformamide such as dimethylformamide or diethylformamide, then phosphorus oxychloride is added to the reaction mixture. The reaction is continued for one to several hours at room temperature.

The resulting compound of the formula (i) may be used either after or without purification for further synthetic reaction.

Method (2): 1,3,7-trisubstituted 5-aminopyrimidopyrimidine derivative obtained by reacting 1,3-disubstituted-(6-amino or 6-halogeno)-5-cyanouracil derivative and a carbamoyl derivative or amidine An uracil derivative having the general formula (v):

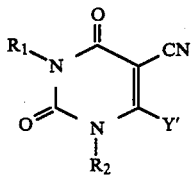

(v)

wherein
$R_1$ is an alkyl group;
$R_2$ is an alkyl or phenyl group; and
$Y'$ is an amino group or a halogen atom;
is reacted with a compound having the general formula (vi):

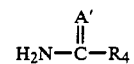

(vi)

wherein
$A'$ is an oxygen atom or an imino group; and
$R_4$ is a hydrogen atom, an alkyl, halogenated lower alkyl, phenyl, amino or lower alkylamino group;
to give an intended compound of the invention having the general formula (vii):

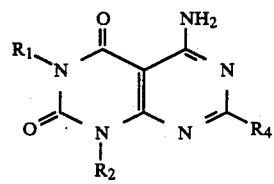

(vii)

wherein
$R_1$ is an alkyl group;
$R_2$ is an alkyl or phenyl group; and
$R_4$ is a hydrogen atom, an alkyl, halogenated lower alkyl, phenyl, amino or lower alkylamino group.

To carry out the above reaction, (a) when $A'$ is an oxygen atom; the reaction is carried out in an appropriate solvent or without using a solvent for one to several hours with heating at an appropriate temperature or under reflux.

(b) when $A'$ is an imino group; the reaction is carried out in an appropriate solvent such as absolute ethanol for one to several hours in the presence of a base such as sodium with heating at an appropriate temperature or under reflux.

Method (3): (5-amino or 5-lower-alkylamino)-1,3-disubstituted pyrimidopyrimidine derivative obtained by reacting 5-cyano-6-di-lower-alkylaminomethyleneaminouracil derivative and an alkylamine or hydroxyamine with optional reduction A compound having the general formula (viii):

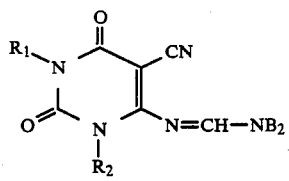

(viii)

wherein
$R_1$ is an alkyl group; and
$R_2$ is an alkyl or phenyl group; and
B is a lower alkyl group having 1 to 4 carbon atoms;
is reacted with a compound having the general formula (ix):

(ix)

wherein
$Z'$ is a lower alkyl or hydroxy group;
to give a compound having the general formula (x):

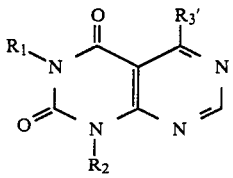

wherein
R₁ is an alkyl group;
R₂ is an alkyl or phenyl group; and
R₃ is an amino or lower alkylamino group.

To carry out the above reaction:
(a) when Z' is a lower alkyl group; the reaction is carried out in an appropriate solvent such as methanol for several hours to several days at room temperature or at an appropriate temperature below room temperature.
(b) when Z' is a hydroxy group; the reaction is carried out in an appropriate solvent such as ethanol in the presence of a base such as triethylamine for one to several hours with heating at an appropriate temperature or under reflux, and then the resulting compound is reduced to give an intended compound of the present invention in the usual way.

In the case of (a), an intermediate having the general formula (xi):

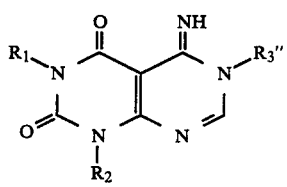

wherein
R₁ is an alkyl group;
R₂ is an alkyl or phenyl group; and
R₃″ is a lower alkyl group;
is produced transiently, and then R₃″ is spontaneously rearranged, i.e. so-called Dimroth rearrangement, to give a compound of the formula (x) wherein R₃' is a lower alkylamino group.

On the other hand, in the case of (b), at first 6-N-oxide having the general formula (xii):

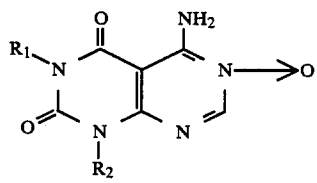

wherein
R₁ is an alkyl group; and
R₂ is an alkyl or phenyl group;
is produced. Then a compound of the formula (xii) is allowed to reduce, e.g. by reacting with triphenylphosphine in a stream of nitrogen with heating, to give a compound of the formula (x) with R₃' being an amino group.

The above mentioned compound of the general formula (viii) can easily be produced as follows:

6-amino-5-cyanouracil derivative having general formula (xiii):

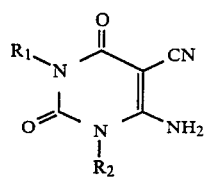

wherein
R₁ is an alkyl group; and
R₂ is an alkyl group or phenyl group; is reacted with di-lower-alkylformamide dialkyl acetal or di-lower-alkylformamide to give 5-cyano-6-di-lower-alkylaminomethyleneaminouracil derivative having the general formula (viii):

To carry out the reaction, a compound of the formula (xiii) is reacted with di-alkyl-formamide dialkylacetal such as dimethylformamide dimethyl acetal, dimethylformamide diethyl acetal, diethylformamide dimethyl acetal or diethylformamide diethyl acetal, or dialkylformamide such as dimethylformamide, in an appropriate solvent such as dimethylformamide, for one to several hours under reflux.

The resulting compound of the formula (viii) may be used either after or without purification for further synthetic reaction.

According to the above mentioned Method (1), pyrimidopyrimidine derivative having a substituent at the 7-position such as an alkyl, halogenated lower alkyl, phenyl, amino or lower alkylamino group can easily be produced, of which the production thereof has been difficult up to now.

That is, any desired substituent can be introduced at the 7-position of the pyrimidopyrimidine skeleton in a one step reaction by reacting with various carbamoyl or; thiocarbamoyl derivatives or amidine. which are provided easily. Moreover, 1,3-disubstituted 6-aminouracil derivatives of the formula (i) as a starting material are synthesized very easily and are stable to deal with when they are isolated. Therefore, the producing Method (1) of the present invention is novel and useful.

According to the above mentioned Method (2), pyrimidopyrimidine derivative having an amino group at the 5-position and a hydrogen atom or an intended substituent at the 7-position can easily be produced by one step. That is, any desired substituent at the 7-position and an amino group at the 5-position can be introduced simultaneously by reacting a 5-cyanouracil derivative and various carbamoyl derivatives or amidine.

Some methods for introducing an amino group into the 5-position of the pyrimidopyrimidine skeleton have been already reported. But the process of the invention is an unknown method that is available for simultaneously introducing both an amino group at the 5-position and hydrogen or an intended substituent at the 7-position combined with ring closure. Furthermore, 5-cyanouracil derivative as a starting material can be provided easily in high yield and the reactants, amides or amidines, can be obtained easily too. Therefore the process for producing the pyrimidopyrimidine derivatives of the invention is novel and extremely useful.

Regarding the above mentioned Method (3), it is a novel process for producing a pyrimidopyrimidine derivative having an amino or alkylamino group at the 5-position. Namely, amino or lower alkylamino substituted at the 5-position can easily be introduced by reacting 5-cyano-6-di-lower-alkylaminomethyleneiminouracil derivatives which can easily be converted from 6-amino-5-cyanouracil, and an amine.

Although some methods available for introducing an amino group through a ring closure reaction have been reported, the process of the invention to introduce an amino or lower alkylamino group has not been known.

The obtained compound of the present invention can be purified in the usual way such as distillation, chromatography or recrystallization. Chemical identification of the compound is established through, inter alia, elementary analysis, melting point, IR, NMR, UV, mass spectrum and so on.

The following examples illustrate the preparation of the compounds of the present invention.

EXAMPLE 1.

(1) 20 g (129 mmol) of 6-amino-1,3-dimethyluracil was suspended in 550 ml of dimethylformamide. 216 g of phosphorus oxychloride was added to the suspension at a temperature below 20° C., and the reaction mixture was stirred for 30 minutes. The resulting precipitate was filtered off and washed with acetone to give 6-imino-1,3-dimethyl-5-dimethylaminomethylene-5,6-dihydrouracil hydrochloride (compound 1) in a 95% yield. The product may also be used in the following reaction without further purification.

m.p.: 206°–210° C.
Elementary Analysis: ($C_9H_{15}ClN_4O_2$).

|  | C % | H % | N % |
| --- | --- | --- | --- |
| Calculated: | 43.82 | 6.13 | 22.71 |
| Found: | 43.30 | 6.16 | 22.66 |

NMR(DMSO-$d_6$) δ=3.12(s,3H), 3.27(s,3H), 3.37(s,3H), 3.62(s,3H), 8.63(s,1H), 9.00(br.s,2H).

(2) After the reaction of 0.5 g (2 mmol) of the compound 1 and 20 mmol of a carbamoyl derivative with heating, either (a) 20 ml of methanol was added to the reaction mixture in order to obtain the precipitate by filtration; or (b) the reaction mixture was dissolved in water followed by extraction with chloroform. The organic layer was dried over anhydrous magnesium sulfate and evaporated to dryness. The obtained crude product was purified by recrystallization.

In accordance with the above procedure, the following compounds were produced. The reaction temperature, reaction time and yield are indicated in parenthesis after the compound name. Also, the solvent for recrystallization is indicated in parenthesis after the m.p.

7-phenyl-1,3-dimethylpyrimido[4,5-d]pyrimidine-2,4-dione (compound 2): (170° C., 2 hours, 71%)

m.p.: 279°–281° C. (ethanol).
Elementary Analysis: ($C_{14}H_{12}N_4O_2$).

|  | C % | H % | N % |
| --- | --- | --- | --- |
| Calculated: | 62.68 | 4.51 | 20.89 |
| Found: | 62.83 | 4.44 | 21.09 |

NMR(CF$_3$COOH) δ=3.60(s,3H), 3.97(s,3H), 7.50–8.10(m,3H), 8.25–8.85(m,2H), 9.63(s,1H).

1,3,7-trimethylpyrimido[4,5-d]pyrimidine-2,4-dione (compound 3): (reflux, 1.3 hours, 71%)

m.p.: 113°–115° C. (ethanol).
Elementary Analysis: ($C_9H_{10}N_4O_2$).

|  | C % | H % | N % |
| --- | --- | --- | --- |
| Calculated: | 52.42 | 4.89 | 27.17 |
| Found: | 52.43 | 4.81 | 27.38 |

NMR(CDCl$_3$) δ=2.81(s,3H), 3.48(s,3H), 3.70(s,3H), 9.23(s,1H).

7-trifluoromethyl-1,3-dimethylpyrimido[4,5-d]pyrimidine-2,4-dione (compound 4): (120° C., 7 hours, 64%)

m.p.: 135°–139° C. (ethanol).
Elementary Analysis: ($C_9H_7F_3N_4O_2$).

|  | C % | H % | N % |
| --- | --- | --- | --- |
| Calculated: | 41.55 | 2.71 | 21.53 |
| Found: | 41.72 | 2.66 | 21.53 |

NMR(CDCl$_3$) δ=3.51(s,3H), 3.76(s,3H), 9.45(s,1H).

1,3-dimethylpyrimido[4,5-d]pyrimidine-2,4-dione (compound 5): (160° C., 4 hours, 92%)

m.p.: 145°–146° C. (water).
Elementary Analysis: ($C_8H_8N_4O_2$).

|  | C % | H % | N % |
| --- | --- | --- | --- |
| Calculated: | 49.99 | 4.20 | 29.16 |
| Found: | 49.88 | 4.22 | 29.06 |

NMR(CDCl$_3$) δ=3.49(s,3H), 3.71(s,3H), 9.16(s,1H), 9.30(s,1H).

EXAMPLE 2.

0.74 g (3 mmol) of compound 1 and 32 mmol of a thiocarbamoyl derivative were refluxed in ethanol with sodium ethoxide prepared from 0.21 g (9 mmol) of sodium and 50 ml of absolute ethanol. Then, the solvent was removed by distillation under reduced pressure and the residue was dissolved in 20 ml of water. The insoluble matter was filtered off and the obtained crude product was purified by recrystallization. In accordance with the above procedure, the following compounds were produced.

7-amino-1,3-dimethylpyrimido[4,5-d]pyrimidine-2,4-dione (compound 6): (reflux, 18 hours, 52%)

m.p.: >300° C. (methanol).
Elementary Analysis: ($C_8H_9N_5O_2$).

|  | C % | H % | N % |
| --- | --- | --- | --- |
| Calculated: | 46.37 | 4.38 | 33.80 |
| Found: | 46.43 | 4.33 | 33.54 |

NMR(DMSO-$d_6$) δ=3.25(s,3H), 3.45(s,3H), 7.66(br.s,2H), 8.69(s,1H).

7-amino-1-phenyl-3-methylpyrimido[4,5-d]pyrimidine-2,4-dione (compound 7): (reflux, 18 hours, 55%)

m.p.: >300° C. (acetonitrile).
Elementary Analysis: ($C_{13}H_{11}N_5O_2$).

|  | C % | H % | N % |
|---|---|---|---|
| Calculated: | 57.98 | 4.12 | 26.01 |
| Found: | 58.16 | 4.00 | 26.11 |

NMR(DMSO-d$_6$)  δ=3.28(s,3H), 7.46(m,7H), 8.76(s,1H).

7-methylamino-1,3-dimethylpyrimido[4,5-d]pyrimidine-2,4-dione (compound 8): (reflux, 15 hours, 70%)

m.p.: 260.5° C. (ethanol).
Elementary Analysis: (C$_9$H$_{11}$N$_5$O$_2$).

|  | C % | H % | N % |
|---|---|---|---|
| Calculated: | 48.86 | 5.01 | 31.66 |
| Found: | 48.72 | 4.90 | 31.77 |

NMR(CF$_3$COOH)  δ=3.22(d,3H,J=4 Hz), 3.48(s,3H), 3.72(s,3H), 8.05(br.s,1H), 8.99(s,1H).

EXAMPLE 3.

3.8 g (32 mmol) of guanidine nitrate and sodium ethoxide which was prepared from 0.51 g (22 mmol) of sodium and 50 ml of absolute ethanol were stirred for 10 minutes in ethanol, and then isoluble sodium nitrate was filtered off. After addition of 0.74 g (3 mmol) of compound 1 to the filtrate, the reaction mixture was refluxed for 2 hours. The resulting precipitate was obtained by filtration and recrystallized from methanol to give the compound 6 in a 81% yield.

EXAMPLE 4.

0.3 g (1.7 mmol) of 6-amino-5-cyano-1,3-dimethyluracil was added to 2 ml of formamide followed by refluxing for 2 hours. 10 ml of water was added to the solution and the crystalline precipitate was filtered off. The crude product was recrystallized from methanol to give 0.2 g of 5-amino-1,3-dimethylpyrimido[4,5-d]pyrimidine-2,4-dione (compound 9) in a 58% yield.

m.p.: >300° C.
Elementary Analysis: (C$_8$H$_9$N$_5$O$_2$).

|  | C % | H % | N % |
|---|---|---|---|
| Calculated: | 46.37 | 4.38 | 33.80 |
| Found: | 46.12 | 4.28 | 33.50 |

NMR(CF$_3$COOH)  δ=3.57(s,3H), 3.83(s,3H), 8.48(br.s,1H), 8.68(s,1H), 9.80(br.s,1H).

6-amino-5-cyano-1,3-diethyluracil or 6-amino-5-cyano-1-iso-butyl-3-methyluracil was employed instead of 6amino-5-cyano-1,3-dimethyluracil to obtain the following compounds in the same manner as above.

5-amino-1,3-diethylpyrimido[4,5-d]pyrimidine-2,4-dione (compound 10): (reflux, 4 hours, 64%)

m.p.: 200°–202° C. (methanol).
Elementary Analysis: (C$_{10}$H$_{13}$N$_5$O$_2$).

|  | C % | H % | N % |
|---|---|---|---|
| Calculated: | 51.05 | 5.57 | 29.77 |
| Found: | 51.26 | 5.57 | 29.49 |

NMR(CDCl$_3$)  δ=1.26(t,3H,J=7 Hz), 1.30(t,3H,J=7 Hz), 4.09(q,2H,J=7 Hz), 4.32(q,2H,J=7 Hz), 6.63(br.s,1H), 8.39(s,1H), 8.63(br.s,1H).

5-amino-1-iso-butyl-3-methylpyrimido[4,5-d]pyrimidine-2,4-dione (compound 11): (reflux, 4 hours, 83%)

m.p.: 192°–193° C. (methanol).
Elementary Analysis: (C$_{11}$H$_{15}$N$_5$O$_2$).

|  | C % | H % | N % |
|---|---|---|---|
| Calculated: | 53.00 | 6.07 | 28.10 |
| Found: | 53.12 | 6.05 | 28.12 |

NMR(CDCl$_3$)  δ=0.94(d,6H,J=7 Hz), 2.26(m,1H), 3.41(s,3H), 4.11(d,2H,J=7 Hz), 6.13(br.s,1H), 8.40(s,1H), 8.58(br.s,1H).

EXAMPLE 5.

0.5 g (2.5 mmol) of 6-chloro-5-cyano-1,3-dimethyluracil and 0.473 g (5 mmol) of acetamidine hydrochloride were added to 50 ml of ethanol containing 0.24 mg of sodium. After reacting under reflux for 1 hour, the crystalline precipitate was filtered off, washed with water and dried. The crude product was recrystallized from acetic acid to give 0.44 g of 5-amino-1,3,7-trimethylpyrimido[4,5-d]pyrimidine-2,4-dione (compound 12) in a 80% yield.

m.p.: 267° C.
Elementary Analysis: (C$_9$H$_{11}$N$_5$O$_2$).

|  | C % | H % | N % |
|---|---|---|---|
| Calculated: | 48.86 | 5.01 | 31.66 |
| Found: | 48.63 | 4.99 | 31.37 |

NMR(CF$_3$COOH)  δ=2.78(s,3H), 3.56(s,3H), 3.82(s,3H).

In the same was as above, benzamidine hydrochloride or guanidine nitrate was employed instead of acetamidine hydrochloride to obtain the following compounds.

5-amino-1,3-dimethyl-7-phenylpyrimido[4,5-d]pyrimidine-2,4-dione (compound 13): (reflux, 1 hour, 61%)

m.p.: 260°266° C. (acetic acid).
Elementary Analysis: (C$_{14}$H$_{13}$N$_5$O$_2$).

|  | C % | H % | N % |
|---|---|---|---|
| Calculated: | 59.35 | 4.63 | 24.72 |
| Found: | 59.20 | 4.51 | 24.96 |

NMR(CF$_3$COOH)  δ=3.60(s,3H), 3.97(s,3H), 7.70(m,3H), 8.30(m,2H).

5,7-diamino-1,3-dimethylpyrimido[4,5-d]pyrimidine-2,4-dione (compound 14): (reflux, 2 hour, 36%)

m.p: >300° C. (acetic acid).
Elementary Analysis: (C$_8$H$_{10}$N$_6$O$_2$).

|  | C % | H % | N % |
|---|---|---|---|
| Calculated: | 43.24 | 4.54 | 37.83 |
| Found: | 43.29 | 4.41 | 37.68 |

NMR(CF$_3$COOH) δ=3.53(s,3H), 3.71(s,3H).

EXAMPLE 6.

(1) 3.6 g (20 mmol) of 6-amino-5-cyano-1,3-dimethyluracil and 9.36 g (80 mmol) of dimethylformamide dimethyl acetal were added to 36 ml of dimethylformamide, and the reaction mixture was refluxed for 30 minutes. The solvent was removed by distillation under reduced pressure. The crude product was crystallized from ether, filtered off, and recrystallized from ethyl acetate to give 4.68 g of 5-cyano-6-dimethylaminomethyleneamino-1,3-dimethyluracil (compound 15) in a 99% yield.

m.p.: 174°–175° C.
Elementary Analysis: ($C_{10}H_{13}N_5O_2$).

|  | C % | H % | N % |
|---|---|---|---|
| Calculated: | 51.06 | 5.57 | 29.77 |
| Found: | 51.33 | 5.64 | 29.67 |

NMR(CF$_3$COOH) δ=3.10(s,3H), 3.15(s,3H), 3.23(s,3H), 3.27(s,3H), 8.26(s,1H).

(2) 0.47 g of the above compound 15 was dissolved in 11 ml of methanol and then 1 ml of methylamine (30% methanol solution) was added dropwise thereto. After stirring overnight at room temperature, the crystalline precipitate was filtered off and recrystallized from ligroin to give 0.38 g of 5-methylamino-1,3-dimethyl-pyrimido[4,5-d]pyrimidine-2,4-dione (compound 16) in a 85% yield.

m.p.: 178°–179° C.
Elementary Analysis: ($C_9H_{11}N_5O_2$).

|  | C % | H % | N % |
|---|---|---|---|
| Calculated: | 48.86 | 5.01 | 31.66 |
| Found: | 48.84 | 5.00 | 31.41 |

NMR(CF$_3$COOH) δ=3.39(d,3H,J=5 Hz), 3.57(s,3H), 3.85(s,3H), 6.80(br.s,1H), 8.65(s,1H).

EXAMPLE 7.

(1) 0.235 g (1 mmol) of the compound 15, 0.138 g (2 mmol) of hydroxyamine hydrochloride and 0.243 g (2.4 mmol) of triethylamine were added to 3 ml of ethanol, and then the reaction mixture was refluxed for 3 hours. After cooling, 5 ml of water was added thereto, and the crystalline precipitate was filtered off and recrystallized from ethanol to give 0.223 g of 5-amino-1,3-dimethyl-pyrimido[4,5-d]pyrimidine-2,4-dione-6-oxide in a 85% yield.

m.p.: 297° C.
Elementary Analysis: ($C_8H_9N_5O_3$).

|  | C % | H % | N % |
|---|---|---|---|
| Calculated: | 43.05 | 4.06 | 31.38 |
| Found: | 42.94 | 4.13 | 31.32 |

NMR(CF$_3$COOH) δ=3.58(s,3H) 3.82(s,3H), 8.27(br.s,1H), 8.87(s,3H), 9.78(br.s,1H).

(2) 0.1 g of the obtained compound was heated at 150° C. with 0.5 g of triphenylphosphine for 30 minutes in a stream of nitrogen.

After cooling, the resulting crude product was washed with ether and recrystallized from acetic acid to give 0.037 g of the compound 9 in a 40% yield.

EXAMPLE 8.

0.92 g of sodium was dissolved in 50 ml of absolute ethanol, and 6.40 g (53 mmol) of guanidine nitrate was added thereto. The solution was stirred for 10 minutes and filtered with Celite filter aid. 0.98 g (4.6 mmol) of 6-amino-1,3-diethyl-5-formyluracil was added to the filtrate and the reaction mixture was refluxed for 24 hours. After removal of the solvent under reduced pressure, 30 ml of water was added thereto. The crystalline precipitate was filtered off and recrystallized from ethanol to give 0.94 g of 7-amino-1,3-diethyl-pyrimido[4,5-d]pyrimidine-2,4-dione (compound 17) in a 87% yield.

m.p.: 230°–232° C.
Elementary Analysis: ($C_{10}H_{13}N_5O_2$).

|  | C % | H % | N % |
|---|---|---|---|
| Calculated: | 51.05 | 5.57 | 29.77 |
| Found: | 50.98 | 5.51 | 29.52 |

NMR(CDCl$_3$+DMSO-d$_6$) δ=1.23(t,3H,J=7 Hz), 1.27(t,3H,J=7 Hz), 4.03(q,2H,J=7 Hz), 4.22(t,3H,J=7 Hz), 6.62(br.s,2H), 8.81(s,1H).

6amino-1-iso-butyl-5-formyl-3-methyluracil was employed instead of 6-amino-1,3-diethyl-5-formyluracil to obtain the following compound in the same manner as above.

7-amino-1-iso-butyl
3-methylpyrimido[4,5-d]pyrimidine-2,4-dione
(compound 18): (reflux, 24 hours, 80%)

m.p.: 249°–250° C. (methanol).
Elementary Analysis: ($C_{10}H_{15}N_5O_2$).

|  | C % | H % | N % |
|---|---|---|---|
| Calculated: | 53.00 | 6.07 | 28.10 |
| Found: | 52.79 | 6.02 | 27.94 |

NMR(DMSO-d$_6$) δ=0.91(d,6H,J=7 Hz), 2.20(m,1H), 3.24(s,3H), 3.94(d,2H,J=7 Hz), 7.42(br.s,2H), 8.69(s,1H).

Compound 17 and compound 18 were also obtained in the same way described in Example 1.

The following descriptions serve to illustrate the pharmaceutical studies of the compounds of the present invention.

(1) Acute toxicity test

The test compounds were administered to groups of 10 ddy-strain male mice (weighing about 20 g). LD$_{50}$ values of the compounds of the invention were calculated by the probit method based on mortality for 7 days after drug administration.

An example of the results is shown in Table 1.

TABLE 1

| Test compound | Route | LD$_{50}$ (mg/kg) |
|---|---|---|
| compound 3 | p.o. | 690 |
| compound 6 | p.o. | 940 |
|  | i.p. | 140 |
| compound 10 | p.o. | 748 |
| compound 12 | p.o. | 707 |
| Theophylline | p.o. | 417 |

(2) Anti-allergic effect

PCA (passive cutaneous anaphylaxis) reaction in rats was taken as an index to an anti-allergic effect of the compound of the present invention.

In order to perform sensitization, anti-DNP-Asc (dinitrophenylated Ascaris extracts) serum diluted with saline was injected intradermally at 4 sites on the shaved back of groups of 10 Wister-strain male rats (6 weeks of age). 1 hour after oral administration of the test drug, the mixture of equivalent amounts of DNP-Asc (5 mg/ml) and 2% Evans blue were intravenously injected to generate PCA reaction. 30 minutes thereafter, rats were killed by decapitation and exsanguinated. The skin was opened in order to evaluate the leakage of blue dye. The obtained skin was dissolved in 2N potassium hydroxide, then 2N phosphoric acid and acetone were added thereto. The amount of dye was determined by measurement of absorbance at 620 nm after centrifugation.

An example of the results is shown in Table 2.

TABLE 2

| Test compound | Dosage (mg/kg) | Leak of Dye (μg/site) | Inhibition (%) |
|---|---|---|---|
| control | — | 10.7 ± 1.0 | — |
| compound 2 | 50 | 8.2 ± 0.9 | 23.4 |
| compound 3 | 50 | 4.2 ± 0.5 | 60.7 |
| compound 4 | 50 | 6.6 ± 1.1 | 38.3 |
| compound 5 | 50 | 4.1 ± 0.8 | 61.7 |
| compound 6 | 20 | 5.0 ± 0.9 | 53.3 |
|  | 50 | 2.3 ± 0.7 | 78.5 |
|  | 100 | 0.7 ± 0.2 | 93.5 |
| compound 7 | 100 | 5.4 ± 0.7 | 49.5 |
| compound 8 | 20 | 7.6 ± 1.6 | 29.0 |
|  | 50 | 2.8 ± 0.7 | 73.8 |
| compound 9 | 20 | 5.9 ± 1.2 | 44.9 |
|  | 100 | 0.6 ± 0.1 | 94.4 |
| compound 10 | 100 | 1.6 ± 0.4 | 85.0 |
| compound 11 | 100 | 2.9 ± 0.8 | 72.9 |
| compound 12 | 100 | 1.0 ± 0.3 | 90.7 |
| compound 14 | 100 | 1.9 ± 0.5 | 82.2 |
| compound 16 | 100 | 1.7 ± 0.6 | 84.1 |
| compound 17 | 100 | 2.4 ± 0.7 | 77.6 |
| compound 18 | 100 | 4.0 ± 0.6 | 62.6 |
| Theophylline | 20 | 3.5 ± 1.3 | 67.3 |

As clearly apparently shown in the above mentioned results, pyrimidopyrimidine derivatives of the present invention have excellent anti-allergic effect which is superior to the conventional drugs, for example, theophylline. Furthermore, the compounds of the invention have low toxicity, so that they are extremely useful with great safety. They are useful as preventive medicine or remedy for various allergic diseases, such as bronchial asthma, urticaria, allergic rhinitis, allergic dermatoses or allergic conjunctivitis. In addition, since the compounds of the present invention can be administered orally, they are of great advantage specially for application with chronic diseases.

The compounds of the present invention can be formulated into pharmaceutical compositions by combination with an appropriate medical carrier or diluent, and into preparations in solid, semisolid, liquid or gaseous form in the usual ways for oral or parenteral administrations.

In pharmaceutical dosage form, the compounds of the present invention can be used in the form of a pharmaceutically acceptable salt, and also can be used alone or with an appropriate active drug, as well as in combination with other pharmaceutically active components.

In case of oral preparation, the compounds can be used alone or combined with an appropriate additive to make tablet, powder, granule or capsule formulations, e.g. with conventional additives such as lactose, mannitol, corn starch or potato starch; with binders such as crystalline cellulose, cellulose derivatives, acacia, corn starch or gelatin; with disintegrators such as corn starch, potato starch or sodium carboxymethylcellulose; with lubricants such as talc or magnesium stearate; and if desired, with diluent, buffering agent, moistening agent, preservative and flavoring agent.

The compounds of the invention can also be made into an ointment by combination with an ointment base such as vaseline, paraffin, plastibase, simple ointment, hydrophilic ointment, hydrophilic vaseline and hydrophilic plastibase.

Furthermore, the compounds of the invention can be made into a suppository by mixing with a variety of bases, e.g. fatty and oily base such as cacao butter, emulsifying base or water-soluble base such as macrogol.

The compounds of the present invention can be formulated into a preparation for injection by dissolving, suspending or emulsifying in aqueous or non-aqueous solvent, such as distilled water for injection, physiologically saline solution, vegetable oil, synthetic aliphatic acid glyceride, esters of higher aliphatic acid or propylene glycol.

In case of inhalation or aerosol preparation, the compounds of the invention in the form of a liquid or minute powder can be filled up in an aerosol container with a gas or liquid spraying agent, and if desired, with conventional adjuvants such as humidifying agent or dispersing agent. They can also be used as a pharmaceutical for a non-pressurized preparation such as in a nebulizer or an atomizer.

In order to make the compounds of the present invention into collyriums, they can be prepared as a solution or suspension together with an aqueous solvent such as sterile purified water and physiologically saline solution; or a non-aqueous solvent for injection.

Cataplasms can be prepared by mixing the compound of the invention with mentha oil, concentrated glycerin, kaolin or other suitable additive.

The desirable dose of pyrimidopyrimidien derivative of the present invention varies with the subject, form of the drug, method and period of administration. However, in order to obtain desirable effects, generally it is recommended to administer orally 1 to 1000 mg, preferably 1 to 500 mg daily. Unit preparations containing appropriate amounts of the compound of the invention are also recommended for administration in 1 to several units daily.

In case of parenteral administration e.g. injections, doses of the compound in the order of one tenth to one third of the above dose are preferable as daily doses.

Some prescription examples of the pharmaceutical composition are shown below as examples which contain the compounds of the invention as active ingredients.

Prescription example 1 (tablet)

| Component | Content in a tablet (mg) |
|---|---|
| compound of this invention | 100 |
| lactose | 130 |
| corn starch | 40 |
| magnesium stearate | 10 |
| Total | 280 mg |

Prescription example 2 (capsule)

| Component | Content in a capsule (mg) |
| --- | --- |
| compound of this invention | 50 |
| lactose | 250 |
| Total | 300 mg |

Prescription example 3 (injection)

| Component | Content in an ampule (mg) |
| --- | --- |
| compound of this invention | 10 |
| sodium chloride | proper amount |
| distilled water for injection | proper amount |
| Total | 1 ml |

Prescription example 4 (ointment)

| Component | Weight (g) |
| --- | --- |
| compound of this invention | 1 |
| emulsified wax | 30 |
| white petrolatum | 50 |
| liquid paraffin | 20 |
| Total | 101 g |

Prescription example 5 (suppository)

| Component | Content in a suppository (mg) |
| --- | --- |
| compound of this invention | 20 |
| cacao butter | 1980 |
| Total | 2000 mg |

Prescription example 6 (inhalation)

| Component | Content in a inhalation (g) |
| --- | --- |
| compound of this invention | 1 |
| lactose | 5 |
| Total | 6 g |

What we claim is:

1. A pyrimidopyrimidine compound of the formula (I):

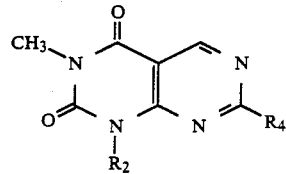

wherein
$R_2$ is an alkyl group having 1 to 3 carbon atoms, and
$R_4$ is an alkyl group having 1 to 3 carbon atoms; a halogenated alkyl group having 1 to 3 carbon atoms, an amino group or an amino group substituted by an alkyl group having 1 to 3 carbon atoms,
or a pharmaceutically acceptable salt thereof.

2. A pyrimidopyrimidine compound according to claim 1, which is 1,3,7-trimethylpyrimido(4,5-d)pyrimidine-2-4-dione.

3. A method for treating mammals suffering from bronchial asthma, urticaria, allergic rhinitis, allergic dermatoses or allergic conjunctivitis which comprises administering thereto a pyrimidopyrimidine compound having the formula (I):

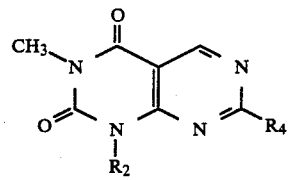

wherein is a lower alkyl group.
$R_4$ is a hydrogen atom, a lower alkyl group, a halogenated lower alkyl group, a phenyl group, an amino group or an amino group substituted by a lower alkyl group;
or a pharmaceutically acceptable salt thereof.

4. An anti-allergic compositions which comprises a pharmaceutically acceptable carrier and an effective anti-allergic pyrimidopyrimidine compound having the formula (I):

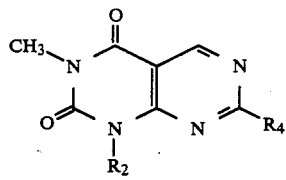

wherein
$R_2$ is an alkyl group having 1 to 3 carbon atoms, and
$R_4$ is an alkyl group having 1 to 3 carbon atoms, a halogenated alkyl group having 1 to 3 carbon atoms, an amino group or an amino group substituted by an alkyl group having 1 to 3 carbon atoms,
or a pharmaceutically acceptable salt thereof.

* * * * *